United States Patent
Helms

(10) Patent No.: US 10,183,057 B2
(45) Date of Patent: *Jan. 22, 2019

(54) USE OF LIPOSOMAL WNT COMPOSITION TO ENHANCE OSSEOINTEGRATION

(71) Applicant: The Board of Trustees of the Leland Stanford Junior University, Stanford, CA (US)

(72) Inventor: Jill Helms, Stanford, CA (US)

(73) Assignee: The Board of Trustees of the Leland Stanford Junior University, Standford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/337,718

(22) Filed: Jul. 22, 2014

(65) Prior Publication Data

US 2014/0371151 A1 Dec. 18, 2014

Related U.S. Application Data

(63) Continuation of application No. 13/199,820, filed on Sep. 9, 2011, now Pat. No. 8,809,272.

(60) Provisional application No. 61/403,122, filed on Sep. 9, 2010.

(51) Int. Cl.
| | | |
|---|---|---|
| A61K 38/17 | (2006.01) | |
| A61K 9/127 | (2006.01) | |
| C07K 14/475 | (2006.01) | |
| A61P 19/08 | (2006.01) | |
| A61K 9/00 | (2006.01) | |

(52) U.S. Cl.
CPC ........ *A61K 38/1709* (2013.01); *A61K 9/0019* (2013.01); *A61K 9/127* (2013.01); *C07K 14/475* (2013.01)

(58) Field of Classification Search
None
See application file for complete search history.

(56) References Cited

U.S. PATENT DOCUMENTS

| | | | |
|---|---|---|---|
| 5,344,654 A * | 9/1994 | Rueger | A61K 9/0024 424/423 |
| 5,589,376 A | 12/1996 | Anderson et al. | |
| 5,654,183 A | 8/1997 | Anderson et al. | |
| 5,672,499 A | 9/1997 | Anderson et al. | |
| 5,750,376 A | 5/1998 | Weiss et al. | |
| 5,824,489 A | 10/1998 | Anderson et al. | |
| 5,849,553 A | 12/1998 | Anderson et al. | |
| 5,851,832 A | 12/1998 | Weiss et al. | |
| 5,851,984 A | 12/1998 | Matthews et al. | |
| 5,968,829 A | 10/1999 | Carpenter | |
| 5,980,885 A | 11/1999 | Weiss et al. | |
| 6,497,872 B1 | 12/2002 | Weiss et al. | |
| 6,777,233 B2 | 8/2004 | Carpenter | |
| 7,115,418 B2 | 10/2006 | Weiss et al. | |
| 7,153,686 B2 | 12/2006 | Uchida et al. | |
| 7,153,832 B2 | 12/2006 | Nusse et al. | |
| 2001/0041743 A1 | 11/2001 | Offenbacher et al. | |
| 2005/0261189 A1 | 11/2005 | Larsen et al. | |
| 2006/0068494 A1 | 3/2006 | Perreault | |
| 2008/0193515 A1 | 8/2008 | Shaughnessy et al. | |
| 2008/0226707 A1 * | 9/2008 | Helms | A61K 9/0019 424/450 |

OTHER PUBLICATIONS

Bienz et al., "Linking colorectal cancer to Wnt signaling," Cell (2000), 103(2):311-320.
Bradley et al., "A soluble form of Wnt-1 protein with mitogenic activity on mammary epithelial cells," Mol. Cell. Biol. (1995), 15(8):4616-4622.
Chenn et al., "Regulation of cerebral cortial size by control of cell cycle exit in neural precursors," Science, 2002, 297:365-369.
Hsieh et al., "Biochemical characterization of Wnt-frizzled interactions using a soluble, biologically active vertebrate Wnt protein," PNAS (1999), 96(7):3546-3551.
"IBMS-ECTS 2005 Abstracts", Bone (2005), 36:S103-S479.
Johnson; et al., "LRP5 and Wnt Signaling: A Union Made for Bone", Journal of Bone and Mineral Research (Nov. 2004), 19(11):1749-1757.
Korinek et al., "Depletion of epithelial stem-cell compartments in the small intestine of mice lacking Tcf-4," Nat Genet. (1998), 19(4):379-383.
Lee et al., "A local Wnt-3a signal is required for development of the mammalian hippocampus," Development (2000), 127(3):457-467.
Lie et al., "Wnt signaling regulates adult hippocampal Neurogenesis," Nature (2005), 437(7063):1370-1375.
Nusse et al., "Many tumors induced by the mouse mammary tumor virus contain a provirus integrated in the same region of the host genome," Cell (1982), 31(1):99-109.
Parkin et al., "Activity of Wnt-1 as a transmembrane protein," Genes Dev. (1993), 7(11):2181-2193.
van de Wetering et al., "The beta-catenin/TCF-4 complex imposes a crypt progenitor phenotype on colorectal cancer cells," Cell (2002),111(2):241-50.

(Continued)

*Primary Examiner* — Xiaozhen Xie

(74) *Attorney, Agent, or Firm* — Pamela J. Sherwood; Bozicevic, Field & Francis LLP

(57) ABSTRACT

Methods and compositions are provided for the therapeutic use of Wnt proteins, for enhancing bone growth and regeneration, including repair following injury, osseointegration of implants, and the like. In some embodiments of the invention, the compositions are administered locally, e.g. by injection at the site of an injury. For certain conditions it is desirable to provide Wnt activity for short periods of time, and an effective dose will be administered over a defined, short period of time.

12 Claims, 7 Drawing Sheets
(7 of 7 Drawing Sheet(s) Filed in Color)
Specification includes a Sequence Listing.

(56) References Cited

OTHER PUBLICATIONS van Leeuwen et al., "Biological activity of soluble wingless protein in cultured *Drosophila* imaginal disc cells," Nature (1994), 368(6469):342-344.
Weissig; et al., "Accumulation of protein-loaded long-circulating micelles and liposomes in subcutaneous Lewis lung carcinoma in mice", Pharmaceutical Research (1998), 15(10):1552-1556.
Willert; et al., "Wnt proteins are lipid-modified and can act as stem cell growth factors", Nature (2002), 423:448-452.

* cited by examiner

USE OF LIPOSOMAL WNT COMPOSITION TO ENHANCE OSSEOINTEGRATION

BACKGROUND OF THE INVENTION

Orthopedic and dental implants are used for a variety of joint and teeth replacements and to promote bone repair in humans and animals, particularly for hip and knee joint and tooth replacements. However, although many individuals experience uncomplicated healing and restoration of function, there is also a high rate of complications, estimated at 10-20% for total joint replacements. The majority of these failures and subsequent revision surgeries are made necessary by failure at the implant-bone interface.

Orthopedic and dental implants are made of materials which are relatively inert ("alloplastic" materials), typically a combination of metallic and ceramic or plastic materials. Previous approaches to improve the outcomes of orthopedic implant surgeries have mainly focused on physical changes to the implant surface that result in increased bone formation. These approaches include using implants with porous metallic surfaces to promote bone ingrowth and spraying implants with hydroxyapatite plasma. Approaches using dental implants have also included the use of topographically-enhanced titanium surfaces in which surface roughness is imparted by a method such as grit blasting, acid etching, or oxidation.

In an effort to promote osseointegration, implant surfaces have undergone major alterations. For example, short peptides containing an arginine-glycine-aspartic acid (RGD) sequences have been attached to implant surfaces because cells utilize RGD sequences to attach to the extracellular matrix. Investigators have attempted to recreate this cell attachment to the modified implant surface but this strategy has resulted in only modest increases in implant osseointegration and mechanical fixation. Alternatively, in an attempt to stimulate blood vessel ingrowth around implants their surfaces have been coated with a coating containing the angiogenic growth factor VEGF.

Another strategy employed to stimulate osseointegration is to nano-texture the implant surface. The rationale behind this strategy is that texturing increases surface area and therefore prevents the implant from "sliding" against cells in the peri-implant environment. In clinical trials, however, nano-texturing does not result in measureable benefits.

The use of protein-based approaches to stimulate implant osseointegration has also been under intense investigation. Bone morphogenetic proteins induce robust endochondral ossification in skeletal fractures and they have also been employed in an effort to stimulate direct bone formation around implants. While in vitro results have been encouraging, in vivo data are less convincing. Recombinant BMPs inhibit osteogenic differentiation of cells in the bone marrow cavity and consequently, are contraindicated for implant osseointegration. See Sykaras et al. (2004) Clin Oral Investig 8(4):196-205; and Minear et al. (2010) Journal of Bone and Mineral Research 25(6):1196-207.

Wnt proteins form a family of highly conserved secreted signaling molecules that regulate cell-to-cell interactions during embryogenesis. Wnt genes and Wnt signaling are also implicated in cancer. Insights into the mechanisms of Wnt action have emerged from several systems: genetics in *Drosophila* and *Caenorhabditis elegans*; biochemistry in cell culture and ectopic gene expression in *Xenopus* embryos. Many Wnt genes in the mouse have been mutated, leading to very specific developmental defects. As currently understood, Wnt proteins bind to receptors of the Frizzled family on the cell surface. Through several cytoplasmic relay components, the signal is transduced to beta-catenin, which then enters the nucleus and forms a complex with TCF to activate transcription of Wnt target genes.

Wnt glycoproteins are thought to function as paracrine or autocrine signals active in several primitive cell types. The Wnt growth factor family includes more than 19 genes identified in the mouse and in humans. The Wnt-1 proto-oncogene (int-1) was originally identified from mammary tumors induced by mouse mammary tumor virus (MMTV) due to an insertion of viral DNA sequence (Nusse and Varmus (1982) Cell 31:99-109). Expression of Wnt proteins varies, but is often associated with developmental process, for example in embryonic and fetal tissues. Wnts may play a role in local cell signaling. Biochemical studies have shown that much of the secreted Wnt protein can be found associated with the cell surface or extracellular matrix rather than freely diffusible in the medium.

Wnt signaling is involved in numerous events in animal development, including the proliferation of stem cells and the specification of the neural crest. Wnt proteins are therefore potentially important reagents in expanding specific cell types, and in treatment of conditions in vivo.

PUBLICATIONS

The biological activity of soluble wingless protein is described in van Leeuwen et al. (1994) Nature 24:368 (6469):342-4. Biochemical characterization of Wnt-frizzled interactions using a soluble, biologically active vertebrate Wnt protein is described by Hsieh et al. (1999) *Proc Natl Acad Sci USA* 96(7):3546-51. Bradley et al. (1995) *Mol Cell Biol* 15(8):4616-22 describe a soluble form of wnt protein with mitogenic activity.

SUMMARY OF THE INVENTION

Methods and compositions are provided for the therapeutic use of Wnt proteins in enhancing osteogenesis, e.g. in accelerating osseointegration of implants, improving bone repair following an injury, in the treatment of bone disease, etc. It is shown herein that a pulse of Wnt activity significantly accelerates bone regeneration by taking advantage of the early Wnt-dependent proliferative effect but avoiding detrimental consequences of persistent Wnt activation. It is also surprisingly found that Wnt in aqueous phase was ineffective in comparison with a formulation where the Wnt protein was inserted in the non-aqueous phase of a lipid structure.

In some embodiments of the invention, the methods provide an individual with a stable orthopedic or dental implant, where the method comprises introducing an orthopedic or dental implant into an individual in need thereof; and contacting the site of the implant with a wnt formulation comprising wnt is inserted in the non-aqueous phase of a lipid structure, where the site of implant includes, without limitation, the peri-implant space. The methods speed osseointegration and extend the functional lifespan of orthopedic and dental implants. This treatment transiently amplifies the normal Wnt response to injury, which occurs after drilling and importantly for this work, implant placement. Advantages include stimulation of osteo-progenitor cell proliferation in peri-implant tissues, e.g. around dental and orthopedic implants, accelerated bone apposition to the implant, leading to faster healing times and stronger osseointegration; and a maintenance of these advantages for extended periods of time. This creates a safety margin for the implant because at any given post surgical time, increasing the bone formation around an implant acts to prevent the failure of that implant upon loading. This safety margin not only protects from implant failure at certain loads, but also allows the implant to be loaded at an earlier time point.

The wnt formulation may be delivered directly to the site of the implant. The wnt formulation is provided immediately before, during or after the implant is introduced, and in some embodiments is delivered within 1, 2, 3, 4, 5, 6, 7 days following introduction. The wnt formulation may be transiently provided over a short, defined period of time, for example as a single bolus, as a continuous injection for a short period of time, e.g. not more than about 48 hours, not more than about 24 hours, not more than about 12 hours, etc., as repeated bolus doses for a short period of time, e.g. not more than about 48 hours, not more than about 24 hours, not more than about 12 hours, etc., and the like.

The methods of the invention may be applied to a wide variety of implants in the orthopedic and dental fields, including, for examples, hip, knee, spine and dental implants. In addition to injection of wnt, the implant may be coated with a wnt formulation of the invention prior to introduction, for example where the implant acts as a receptacle for the formulation, which is extruded or released at the appropriate time after initial inflammation has subsided; where a reservoir of the wnt formulation is implanted in conjunction with the implant, and the like.

In some embodiments of the invention, a pharmaceutical composition for in vivo administration to enhance osteogenesis comprises a therapeutically effective dose of a Wnt protein, where the Wnt protein is inserted in the non-aqueous phase of a lipid structure, e.g. in the surface of a liposome, micelle, lipid raft, etc., in an emulsion, and the like. In some embodiments the Wnt protein is presented in its active conformation on an outer liposome membrane or micelle. Where the lipid structure is a liposome it is desirable that the Wnt protein not be encapsulated within the liposome, e.g. in an aqueous phase. The lipid-containing particles typically display copies of a wnt polypeptide, the particles comprising at least one copy of a wnt polypeptide bearing at least one lipid moiety, where the composition contains at least 50% of the Wnt polypeptides displayed on the exterior surface of the particle.

In some embodiments of the invention, the Wnt protein is a mammalian protein, including, without limitation, human Wnt proteins, e.g. Wnt3A. The Wnt compositions find use in a variety of therapeutic methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Bone implants have been extensively employed to replace missing or damaged hard tissues. Implants are manufactured to withstand the movement and stress associated with these clinical applications but the lifespan of implants is limited: Because they are denser and stronger than bone, implants can eventually weaken the surrounding bone-material interface. When this connection between bone and the implant surface is lost then the implant must be removed and replaced. In cases where osseointegration is likely to be compromised because of a poor implant bed or underlying illness then the ability to stimulate rapid and robust osseointegration is essential. Consequently, considerable effort has gone into developing techniques that enhance and maintain osseointegration of implants. Osseointegration occurs when cells in the peri-implant space attach to the implant surface and differentiate into matrix-secreting osteoblasts.

In some embodiments of the invention, methods are providing for providing an individual with a stable orthopedic or dental implant, where the method comprises introducing an orthopedic or dental implant into an individual in need thereof; and contacting the site of the implant with a wnt formulation comprising wnt is inserted in the non-aqueous phase of a lipid structure, where the site of implant includes, without limitation, the peri-implant space. The methods speed osseointegration and extend the functional lifespan of orthopedic and dental implants.

The methods of the invention provide important benefits in the field of orthopedic and dental implants. Implant stability is a function of two general characteristics: the geometry of the implant and the amount and quality of the bone in which the implant is placed. When either of these features is sub-optimal then forces, even forces that are relatively small, can cause excessive displacement of the implant within the implant bed. Excessive displacement causes implant motion and if this motion is disproportionately large then the implant is considered non-functional and must be removed.

Precisely what constitutes an excessive force, however, is difficult to define. One reason for this problem is that the material properties of the implant bed are continually changing: Initially, the peri-implant space is filled with a fibrin-rich blood clot that has a low modulus of elasticity. Consequently, even a very small force, F, will cause a large displacement of the implant that in turn creates very high interfacial strains. When this strain/force passes a certain threshold then peri-implant cells tend to arrest their differentiation into osteoblasts and form fibrous or fibrocartilaginous tissue instead.

Figure 4:
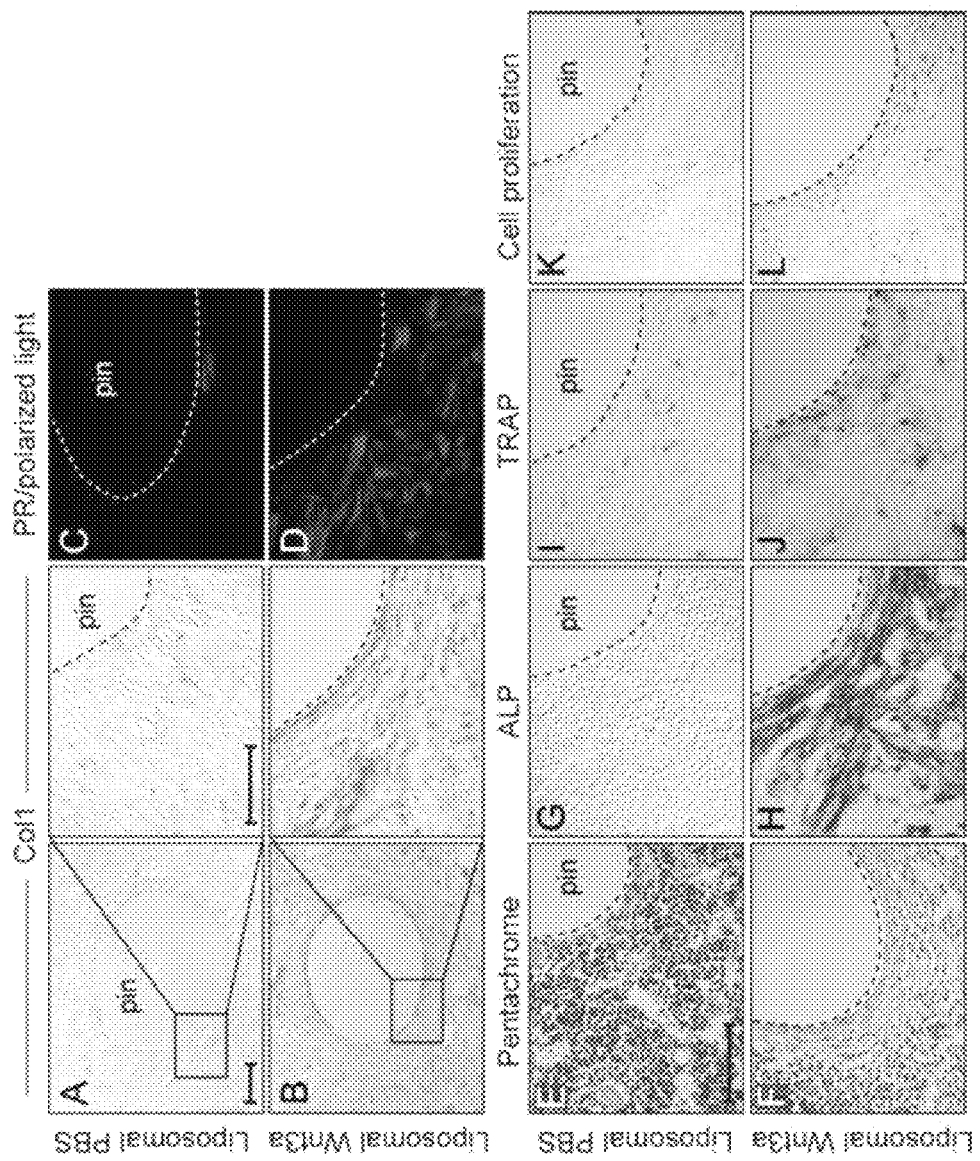
FIG. 4: Liposomal Wnt3a accelerates matrix mineralization and bone remodeling. Forty-eight hours after treatment, A) in situ hybridization for Collagen type I (Col1) was performed on tissues treated with liposomal PBS, or B) liposomal Wnt3a. C) Picrosirius red staining for collagen matrix after treatment with liposomal PBS or D) liposomal Wnt3a. E) Pentachrome histology, in which bone matrix stains yellow, seen treatment with liposomal PBS or F) liposomal Wnt3a. G) Alkaline phosphatase (ALP) activity after liposomal PBS or H) liposomal Wnt3a. I) Tartrate resistance acid phosphatase (TRAP) activity after liposomal PBS or J) liposomal Wnt3a. K) Proliferating cell nuclear antigen (PCNA) staining after liposomal PBS or L) liposomal Wnt3a. Scale bar for panels A and B=100 µm, all other panels=50 µm.

As the peri-implant tissue matures, the space becomes populated by cells that differentiate into osteoblasts and deposit a collagen-rich extracellular matrix (see, for example, FIG. 4C,D). This collagen-rich matrix will have a higher modulus of elasticity than the fibrin clot, meaning that the same force, F, will elicit considerably less displacement of the implant and create significantly lower interfacial strains. Within a certain range (e.g., 10-30%) these strains resulting from implant loading can act as osteogenic stimuli.

In the final stages of implant osseointegration, the mineralized peri-implant matrix undergoes remodeling through a process of mineral apposition and osteoclastic activity that eventually transforms the woven bone into lamellar bone (see, for example, FIG. 6H,I). At this point, the implant is most resistant to excessive displacement. It is apparent from the clinical literature and from biomechanical testing that the sooner the implant is stabilized by interfacial bone, the more force the implant can withstand without adverse effects.

The methods of the invention utilize therapeutic Wnt protein formulations. In some embodiments of the invention, a pharmaceutical composition for in vivo administration is provided, comprising a therapeutically effective dose of a Wnt protein, where the Wnt protein is inserted in the non-aqueous phase of a lipid structure, e.g. in the surface of a liposome, micelle, lipid raft, etc., in an emulsion, and the like. In some embodiments the Wnt protein is presented in its active conformation on an outer liposome membrane or micelle. Pharmaceutical compositions of the present invention can be administered to an animal for therapeutic purposes. In some embodiments of the invention, the compositions are administered locally, e.g. by injection at the site of an injury.

In some embodiments of the invention, a pharmaceutical composition of the present invention is administered to an animal to accelerate bone growth, e.g. to enhance osseointegration of dental or orthopedic implants, following an injury, in the treatment of bone disease, etc.

Biologically active Wnt pharmaceutical compositions retain the effector functions that are directly or indirectly caused or performed by native sequence Wnt polypeptides when administered in vivo. Effector functions of native sequence Wnt polypeptides include stabilization of β-catenin, stimulation of stem cell self-renewal, and the like.

The Wnt compositions find use in a variety of therapeutic methods, including the maintenance and growth of stem cells, tissue regeneration, and the like.

For use in the above methods, the invention also provides an article of manufacture, comprising: a container, a label on the container, and a composition comprising an active agent within the container, wherein the composition comprises substantially homogeneous biologically active Wnt protein inserted in the non-aqueous phase of a lipid structure, which is effective in vivo, for example in enhancing proliferation and/or maintenance of stem or progenitor cells, and the label on the container indicates that the composition can be used for enhancing proliferation and/or maintenance of those cells.

DEFINITIONS

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

Orthopaedic and Dental Biomaterial and Implants.

Orthopaedic and dental biomaterials can be implanted into or near bones to facilitate healing or to compensate for a lack or loss of bone tissue. The materials used in orthopaedic surgery include, for example, ceramics; polymers; metals, such as stainless steel, cobalt-chromium and titanium; and restorable materials, such as biogas, various modifications of hydroxyapatite and bone grafts. Polyethylene and polymethylmethacrylate are commonly used in joints such as knee, elbow and hip replacements.

Wnt Protein.

Wnt proteins form a family of highly conserved secreted signaling molecules that regulate cell-to-cell interactions during embryogenesis. The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides. In some embodiments of the invention, the Wnt protein comprises palmitate covalently bound to a cysteine residue.

A "native sequence" polypeptide is one that has the same amino acid sequence as a Wnt polypeptide derived from nature. Such native sequence polypeptides can be isolated from cells producing endogenous Wnt protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, and the like.

The term "native sequence Wnt polypeptide" includes human and murine Wnt polypeptides. Human wnt proteins include the following: Wnt 1, Genbank reference NP_005421.1; Wnt 2, Genbank reference NP 003382.1, which is expressed in brain in the thalamus, in fetal and adult lung and in placenta; two isoforms of Wnt 2B, Genbank references NP_004176.2 and NP_078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell-cell signaling during morphogenesis of the developing neural tube, and have the Genbank references NP_110380.1 and X56842. Wnt3A is expressed in bone marrow. Wnt 4 has the Genbank reference NP_110388.2. Wnt 5A and Wnt 5B have the Genbank references NP_003383.1 and AK013218. Wnt 6 has the Genbank reference NP_006513.1; Wnt 7A is expressed in placenta, kidney, testis, uterus, fetal lung, and fetal and adult brain, Genbank reference NP_004616.2. Wnt 7B is moderately expressed in fetal brain, weakly expressed in fetal lung and kidney, and faintly expressed in adult brain, lung and prostate, Genbank reference NP_478679.1. Wnt 8A has two alternative transcripts, Genbank references NP_114139.1 and NP_490645.1. Wnt 8B is expressed in the forebrain, and has the Genbank reference NP_003384.1. Wnt 10A has the Genbank reference NP_079492.2. Wnt 10B is detected in most adult tissues, with highest levels in heart and skeletal muscle. It has the Genbank reference NP_003385.2. Wnt 11 is expressed in fetal lung, kidney, adult heart, liver, skeletal muscle, and pancreas, and has the Genbank reference NP_004617.2. Wnt 14 has the Genbank reference NP_003386.1. Wnt 15 is moderately expressed in fetal kidney and adult kidney, and is also found in brain. It has the Genbank reference NP_003387.1. Wnt 16 has two isoforms, Wnt-16a and Wnt-16b, produced by alternative splicing. Isoform Wnt-16B is expressed in peripheral lymphoid organs such as spleen, appendix, and lymph nodes, in kidney but not in bone marrow. Isoform Wnt-16a is expressed at significant levels only in the pancreas. The Genbank references are NP_057171.2 and NP_476509.1.

The term "native sequence Wnt protein" includes the native proteins with or without the initiating N-terminal methionine (Met), and with or without the native signal sequence. The native sequence human and murine Wnt polypeptides known in the art are from about 348 to about 389 amino acids long in their unprocessed form reflecting variability (particularly at the poorly conserved amino-terminus and several internal sites), contain 21 conserved cysteines, and have the features of a secreted protein. The molecular weight of a Wnt polypeptide is about 38-42 kD.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric" Wnt polypeptide is a polypeptide comprising a Wnt polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, combine a portion of the Wnt polypeptide with an immunoglobulin sequence, and epitope tagged polypeptides, which comprise a Wnt polypeptide or portion thereof fused to a "tag polypeptide". The tag polypeptide has enough residues to provide an epitope against which an antibody can be made, yet is short enough such that it does not interfere with biological activity of the Wnt polypeptide. Suitable tag polypeptides generally have at least six amino acid residues and usually between about 6-60 amino acid residues.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

Biologically Active Wnt.

The methods of the present invention provide for Wnt compositions that are active when administered to an animal, e.g. a mammal, in vivo. One may determine the specific activity of a Wnt protein in a composition by determining the level of activity in a functional assay after in vivo administration, e.g. accelerating bone regeneration, upregulation of stem cell proliferation, etc., quantitating the amount of Wnt protein present in a non-functional assay, e.g. immunostaining, ELISA, quantitation on coomasie or silver stained gel, etc., and determining the ratio of in vivo biologically active Wnt to total Wnt.

Lipid Structure.

As used in the methods of the invention, lipid structures are found to be important in maintaining the activity of wnt proteins following in vivo administration. The wnt proteins are not encapsulated in the aqueous phase of these structures, but are rather integrated into the lipid membrane, and may be inserted in the outer layer of a membrane. Such a structure is not predicted from conventional methods of formulating proteins in, for example, liposomes.

The methods used for tethering wnt proteins to the external surface of a liposome or micelle may utilize a sequence so as to emphasize the exoliposomal display of the protein, where crude liposomes are first pre-formed; wnt protein is then added to the crude mixture, which will favor addition of exo-liposomal wnt, followed by various formulation steps, which may include size filtering; dialysis, and the like Suitable lipids include fatty acids, neutral fats such as triacylglycerols, fatty acid esters and soaps, long chain (fatty) alcohols and waxes, sphingoids and other long chain bases, glycolipids, sphingolipids, carotenes, polyprenols, sterols, and the like, as well as terpenes and isoprenoids. For example, molecules such as diacetylene phospholipids may find use.

Included are cationic molecules, including lipids, synthetic lipids and lipid analogs, having hydrophobic and hydrophilic moieties, a net positive charge, and which by itself can form spontaneously into bilayer vesicles or micelles in water. The term also includes any amphipathic molecules that can be stably incorporated into lipid micelle or bilayers in combination with phospholipids, with its hydrophobic moiety in contact with the interior, hydrophobic region of the micelle or bilayer membrane, and its polar head group moiety oriented toward the exterior, polar surface of the membrane.

The term "cationic amphipathic molecules" is intended to encompass molecules that are positively charged at physiological pH, and more particularly, constitutively positively charged molecules, comprising, for example, a quaternary ammonium salt moiety. Cationic amphipathic molecules typically consist of a hydrophilic polar head group and lipophilic aliphatic chains. Similarly, cholesterol derivatives having a cationic polar head group may also be useful. See, for example, Farhood et al. (1992) *Biochim. Biophys. Acta* 1111:239-246; Vigneron et al. (1996) *Proc. Natl. Acad. Sci.* (USA) 93:9682-9686.

Cationic amphipathic molecules of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Solodin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chem. 10:261-271), DMRIE (Feigner et al., (1994) J. Biol. Chem. 269(4): 2550-2561), EDMPC (commercially available from Avanti Polar Lipids, Alabaster, Ala.), DCChol (Gau and Huang (1991) Biochem. Biophys. Res. Comm. 179:280-285), DOGS (Behr et al., (1989) Proc. Natl. Acad. Sci. USA, 86:6982-6986), MBOP (also called MeBOP) (WO 95/14651), and those described in WO 97/00241.

While not required for activity, in some embodiments a lipid structure may include a targeting group, e.g. a targeting moiety covalently or non-covalently bound to the hydrophilic head group. Head groups useful to bind to targeting moieties include, for example, biotin, amines, cyano, carboxylic acids, isothiocyanates, thiols, disulfides, α-halocarbonyl compounds, α,β-unsaturated carbonyl compounds, alkyl hydrazines, etc.

Chemical groups that find use in linking a targeting moiety to an amphipathic molecule also include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hyrodrazone, lipids, and the like, as known in the art.

For example, targeting molecules may be formed by converting a commercially available lipid, such as DAGPE, a PEG-PDA amine, DOTAP, etc. into an isocyanate, followed by treatment with triethylene glycol diamine spacer to produce the amine terminated thiocarbamate lipid which by treatment with the para-isothiocyanophenyl glycoside of the targeting moiety produces the desired targeting glycolipids. This synthesis provides a water soluble flexible linker molecule spaced between the amphipathic molecule that is integrated into the nanoparticle, and the ligand that binds to cell surface receptors, allowing the ligand to be readily accessible to the protein receptors on the cell surfaces.

A targeting moiety, as used herein, refers to all molecules capable of specifically binding to a particular target molecule and forming a bound complex as described above. Thus the ligand and its corresponding target molecule form a specific binding pair.

The term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

Examples of targeting moieties include, but are not limited to antibodies, lymphokines, cytokines, receptor proteins such as CD4 and CD8, solubilized receptor proteins such as soluble CD4, hormones, growth factors, peptidomimetics, synthetic ligands, and the like which specifically bind desired target cells, and nucleic acids which bind corresponding nucleic acids through base pair complementarity. Targeting moieties of particular interest include peptidomimetics, peptides, antibodies and antibody fragments (e.g. the Fab' fragment). For example, β-D-lactose has been attached on the surface to target the aloglysoprotein (ASG) found in liver cells which are in contact with the circulating blood pool.

Cellular targets include tissue specific cell surface molecules, for targeting to specific sites of interest, e.g. neural cells, liver cells, bone marrow cells, kidney cells, pancreatic cells, muscle cells, and the like. For example, nanoparticles targeted to hematopoietic stem cells may comprise targeting moieties specific for CD34, ligands for c-kit, etc. Nanoparticles targeted to lymphocytic cells may comprise targeting moieties specific for a variety of well known and characterized markers, e.g. B220, Thy-1, and the like.

The use of liposomes or micelles as a delivery vehicle is one method of interest. A liposome is a spherical vesicle with a membrane composed of a phospholipid bilayer. Liposomes can be composed of naturally-derived phospholipids with mixed lipid chains (like egg phosphatidylethanolamine), or of pure surfactant components like DOPE (dioleolylphosphatidylethanolamine). Liposomes often contain a core of encapsulated aqueous solution; while lipid spheres that contain no aqueous material are referred to as micelles. As the wnt proteins are present in the lipid phase and not the encapsulated aqueous phase, micelles may be used interchangeably with liposome for the compositions of the present invention. The lipids may be any useful combination of known liposome or micelle forming lipids, including cationic lipids, such as phosphatidylcholine, or neutral lipids, such as cholesterol, phosphatidyl serine, phosphatidyl glycerol, and the like.

In another embodiment, the vesicle-forming lipid is selected to achieve a specified degree of fluidity or rigidity, to control the stability of the structure in serum, etc. Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures. Lipid fluidity is achieved by incorporation of a relatively fluid lipid, typically one having a lipid phase with a relatively low liquid to liquid-crystalline phase transition temperature, e.g., at or below room temperature.

The liposomes may be prepared by a variety of techniques, such as those detailed in Szoka, F., Jr., et al., Ann. Rev. Biophys. Bioeng. 9:467 (1980). Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The liposomes micelles, etc. of the invention may have substantially homogeneous sizes in a selected size range, typically between about 0.01 to 0.5 microns, more preferably between 0.03-0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less.

The pharmaceutical compositions of the present invention also comprise a pharmaceutically acceptable carrier. Many pharmaceutically acceptable carriers may be employed in the compositions of the present invention. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of lipid structures in the carrier may vary. Generally, the concentration will be about 0.1 to 1000 mg/ml, usually about 1-500 mg/ml, about 5 to 100 mg/ml, etc. Persons of skill may vary these concentrations to optimize treatment with different lipid components or of particular patients.

Compositions will comprise a therapeutically effective in vivo dose of a wnt protein, and may comprise a cocktail of one or more wnt proteins.

THERAPEUTIC METHODS

Methods are providing for providing an individual with a stable orthopedic or dental implant, where the method comprises introducing an orthopedic or dental implant into an individual in need thereof; and contacting the site of the implant with a wnt formulation comprising wnt is inserted in the non-aqueous phase of a lipid structure, where the site of implant includes, without limitation, the peri-implant space. The methods speed osseointegration and extend the functional lifespan of orthopedic and dental implants.

The wnt formulation may be delivered directly to the site of the implant. The wnt formulation is provided immediately before, during or after the implant is introduced, and in some embodiments is delivered within 1, 2, 3, 4, 5, 6, 7 days following introduction of the implant. The wnt formulation may be transiently provided over a short, defined period of time, for example as a single bolus, as a continuous injection for a short period of time, e.g. not more than about 48 hours, not more than about 24 hours, not more than about 12 hours, etc., as repeated bolus doses for a short period of time, e.g. not more than about 48 hours, not more than about 24 hours, not more than about 12 hours, etc., and the like.

The methods of the invention may be applied to a wide variety of implants in the orthopedic and dental fields, including, for examples, hip, knee, spine and dental implants. In addition to injection of wnt, the implant may be coated with a wnt formulation of the invention prior to introduction, for example where the implant acts as a receptacle for the formulation, which is extruded or released at the appropriate time after initial inflammation has subsided; where a reservoir of the wnt formulation is implanted in conjunction with the implant, and the like.

The subject methods are useful for both prophylactic and therapeutic purposes. Thus, as used herein, the term "treating" is used to refer to stabilization of implants, prevention of implant failure, and treatment of a pre-existing condition. Evidence of therapeutic effect may be any diminution in the severity of disease. The therapeutic effect can be measured in terms of clinical outcome or can be determined by immunological or biochemical tests. Patents for treatment may be mammals, e.g. primates, including humans, may be laboratory animals, e.g. rabbits, rats, mice, etc., particularly for evaluation of therapies, horses, dogs, cats, farm animals, etc.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

In some embodiments of the invention, administration of the wnt pharmaceutical formulation is performed by local administration. Local administration, as used herein, may refer to topical administration, but more often refers to injection or other introduction into the body at a site of treatment. Examples of such administration include injection at the site of an implant or bone weakness, and the like. It is found that the lipid structures of the present invention generally are less effective when systemically administered, and the highest activity may be found at or around the site where it is initially introduced.

In some embodiments of the invention, the formulations are administered on a short term basis, for example a single administration, or a series of administration performed over, e.g. 1, 2, 3 or more days, up to 1 or 2 weeks, in order to obtain a rapid, significant increase in activity. The size of the dose administered must be determined by a physician and will depend on a number of factors, such as the nature and gravity of the disease, the age and state of health of the patient and the patient's tolerance to the drug itself.

In many clinical situations, the bone healing condition are less ideal due to decreased activity of bone forming cells, e.g. within aged people, following injury, in osteogenesis imperfecta, etc. Within bone marrow stroma there exists a subset of non-hematopoietic cells capable of giving rise to multiple cell lineages. These cells termed as mesenchymal stem cells (MSC) have potential to differentiate to lineages of mesenchymal tissues including bone, cartilage, fat, tendon, muscle, and marrow stroma.

A variety of bone and cartilage disorders affect aged individuals. Such tissues are normally regenerated by mesenchymal stem cells. Included in such conditions is osteoarthritis. Osteoarthritis occurs in the joints of the body as an expression of "wear-and-tear". Thus athletes or overweight individuals develop osteoarthritis in large joints (knees, shoulders, hips) due to loss or damage of cartilage. This hard, smooth cushion that covers the bony joint surfaces is composed primarily of collagen, the structural protein in the body, which forms a mesh to give support and flexibility to the joint. When cartilage is damaged and lost, the bone surfaces undergo abnormal changes. There is some inflammation, but not as much as is seen with other types of arthritis. Nevertheless, osteoarthritis is responsible for considerable pain and disability in older persons.

In conditions of the aged where repair of mesenchymal tissues is decreased, or there is a large injury to mesenchymal tissues, the stem cell activity may be enhanced by administration of tissue regenerating agent(s).

In methods of accelerating bone repair, a pharmaceutical wnt composition of the present invention is administered to a patient suffering from damage to a bone, e.g. following an injury, or desiring increased osteogenic acitivity, e.g. at the site of an implant. The formulation is preferably administered at or near the site of desired osteogenesis, following the incident requiring bone regeneration. The wnt formulation is preferably administered for a short period of time, and in a dose that is effective to increase the number of bone progenitor cells present at the site of injury. In some embodiments the wnt is administered within about four days, three days, two days, usually within about 1 day of implantation or injury, and is provided for not more than about two weeks, not more than about one week, not more than about 5 days, not more than about 4 days, not more than 3 days, etc.

In an alternative method, patient suffering from damage to a bone is provided with a composition comprising bone marrow cells, e.g. a composition including mesenchymal stem cells, bone marrow cells capable of differentiating into osteoblasts; etc. The bone marrow cells may be treated ex vivo with a pharmaceutical composition comprising a wnt protein or proteins in a dose sufficient to enhance regeneration; or the cell composition may be administered to a patient in conjunction with a wnt formulation of the invention.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

EXPERIMENTAL

Example 1

A protein-based strategy to stimulate implant osseointegration is provided. A pro-osteogenic effect is achieved by Wnt signals that promote osteoblast activation, inhibit osteoclast activity, and stimulate the differentiation of pluripotent stem cells towards an osteoblast cell fate.

Methods and Materials

In Vivo Wnt Responsiveness.

Axin2$^{LacZ/+}$ mice were bred as described and the LacZ product, ß-galactosidase, was detected by X-gal staining. Tissues were embedded in OCT followed by cryo-sectioning, then fixed with 0.2% glutaraldehyde for 15 min and stained with Xgal overnight at 37° C.

Implant Surgery.

All procedures followed protocols approved by the Stanford Committee on Animal Research. Adult mice (males, between 3-5 months old) were anaesthetized with an intraperitoneal injection of Ketamine/Xylazine. An incision was made over the right anterior-proximal tibia and the tibial surface of the knee was exposed while the periosteal surface was preserved. A stainless steel needle (Precision glide Needle 27½, Beckton Dickinson, NJ) with diameter of 0.4 mm was cut to obtain a 6 mm length, and the top of the needle was bent at a 90° angle approximately 1 mm down. The needle was used as an implant in our model and was carefully driven through the knee into the bone marrow of the tibia. Lastly, the wounds were sutured closed with non-absorbable sutures and antibiotics and analgesics were subsequently given to the animals. Animals were housed in a temperature-controlled environment with 12-hour light dark cycles and were given food and water ad libitum.

Molecular and Cellular Assays.

Under RNase-free conditions tibiae were harvested, the skin and outer layers of muscle were removed, the tissues washed in 1×PBS at 4° C. and then fixed in 4% paraformaldehyde. The implant was carefully removed and the tissues were decalcified in a heat-controlled microwave in 19% EDTA, after which the tibia was prepared for paraffin embedding. Paraffin embedding followed standard protocols and sections were generated at an 8-µm thickness. For in situ hybridization, the relevant digoxigenin-labeled mRNA antisense probes were prepared from cDNA templates for Runx2, Collagen type I, Collagen type IV and Osteocalcin. Sections were de-waxed, treated with Proteinase K, and incubated in hybridization buffer containing the relevant riboprobe. Probe was added at an approximate concentration of 0.25 µg/mL. Stringency washes of saline sodium citrate solution were done at 52° C., and further washed in maleic acid buffer with 1% Tween 20. Slides were treated with Anti-DIG antibody (Roche). For color detection, slides were incubated in nitro blue tetrazolium chloride (NBT; Roche) and 5-bromo-4-chloro-3-indolyl phosphate (BCIP; Roche). After developing, the slides were cover-slipped with aqueous mounting medium. For immunostaining, tissue sections were de-waxed followed by immersion in $H_2O_2$/PBS, washed in PBS, incubated in ficin (Zymed), treated with 0.1 M glycine, washed further, and then blocked in ovalbumin (Worthington) and 1% whole donkey IgG (Jackson ImmunoResearch). Appropriate primary antibody was added and incubated overnight at 4° C., then washed in PBS. Samples were incubated with peroxidase-conjugated secondary antibody (Jackson ImmunoResearch) for an hour and a DAB substrate kit (Vector Laboratories) was used to develop the color reaction. Some commonly used antibodies include proliferating cell nuclear antigen (PCNA, Zymed) and platelet endothelial cell adhesion molecule 1 (PECAM-1, BD Biosciences). For tartrate-resistant acid phosphatase (TRAP) staining, tissue sections were de-waxed and then treated with a TRAP staining kit (Sigma).

Histology and Histomorphometric Analyses.

Pentachrome and aniline blue staining were performed; slides were mounted with Permount after dehydration in a series of ethanol and xylene. To quantify new bone, the 1.0 mm circular mono-cortical defect was represented across approximately 160, 8 µm-thick tissue sections. Out of those 160 sections we used a minimum of 6 slides (4 sections/slide) to quantify the amount of aniline blue-stained new osteoid matrix. Tissue sections were photographed using a Leica digital imaging system (5× objective). The resulting digital images were analyzed with Adobe Photoshop CS2 software. We chose a fixed, rectangular region of interest (ROI) that in all images corresponded to $10^6$ pixels. The injury site was always represented inside this ROI by manually cropping the correct size and position of each image. Aniline blue-positive pixels were automatically selected using the magic wand tool set to a color tolerance of 60. This tolerance setting resulted in highlighted pixels with a range of blue that corresponded precisely with the histological appearance of new osteoid tissue in the aniline blue-stained sections. Cortical surfaces, or bone fragments resulting from the drill injury, were manually deselected. The total number of aniline blue-positive pixels for each section was then recorded. The pixel counts from individual sections were averaged for each tibia sample and the differences within and among treatment groups were calculated based on these averages.

Liposomal Preparation and Delivery.

1,2-Dimyristoyl-sn-Glycero-3-Phosphocholine (DMPC; Sigma, cat #850345C) in chloroform was dried to a thin film in a 10 mL round bottom flask. Purified Wnt3a with a concentration of 1-1.3 µg/mL was mixed with dried DMPC. The lipid-Wnt3a solution was extruded 40 times through a 100-200 nm polycarbonate membrane in a thermo-barrel extruder, keeping the temperature constant at 30-32° C. (Avanti Polar Lipids, Inc). The supernatant was removed and the liposome pellet was re-suspended in 1×DMEM (Mediatech, Inc., Herndon, Va.). Liposomes were stored at 4° C. and used within 10 days of preparation. The liposomal preparation had an effective Wnt3a concentration between 0.8-1.0 µg/mL, and a single (104) dose of this solution was delivered to the injury site by injection.

Mono-cortical tibial defects were treated with liposomal Wnt3a preparation (L-Wnt3a) by injecting 10 µL of liposomal Wnt3a into the injury site at post-surgical day 3. An incision was made over the right anterior-proximal tibia and the knee was exposed. Liposomes were injected by driving a needle through the knee adjacent to the implant. The wounds were closed with non-absorbable sutures.

RT-PCR.

For gene expression analyses, tissues were homogenized in TRIzol® (Invitrogen), and RNA was isolated using RNeasy® mini column (Qiagen). Reverse transcription was performed using SuperScript III First-Strand Synthesis SuperMix for RT-PCR (Invitrogen). PCR reactions were performed and monitored using StepOnePlus Real-Time PCR System. Normalized expression levels reported were calculated based on differences between threshold cycles for the gene of interest, and the house-keeping gene ß-actin. The following primer sets were used: ß-actin, sense 5'-ggaatgggtcagaaggactc-3' (SEQ ID NO:10), antisense 5'-CATGTCGTCCAGTTGGTAA-3' (SEQ ID NO:1); Ki67 sense 5'-GCCAGCCCCGCTGATACACC-3' (SEQ ID NO:2) antisense 5'-TTCCCTGGAGACTGGGGCCA-3' (SEQ ID NO:3), Collagen type I, sense 5'-GCCTCCCA-GAACATCACCTAT-3' (SEQ ID NO:4), antisense 5'-AAT-TCCTGGTCTGGGGCA-3' (SEQ ID NO:5) and Runx2, sense 5'-ATTAACCCTCACTAAAGGGACCCACGGC-CCTCCCTGAACT-3' (SEQ ID NO:6), antisense 5'-TAATACGACTCACTATAGGGGCCGAGGGACAT-GCCTGACG-3' (SEQ ID NO:7). In Axin2$^{LacZ/+}$ mice, the following primers were used: sense 5'-TTGATAAGGTC-CTGGCAACTC-3' (SEQ ID NO:8); antisense 5'-GC-GAACGGCTGCTTATTT-3' (SEQ ID NO:9).

Statistical Analyses.

A Student's t-test was used to test for significant differences between data sets. To create histograms the means of data sets were calculated, and error bars in histograms represented standard deviation. P-values under 0.05 were considered significant.

Results

Endogenous Wnt Signaling and Endosteal Bone Homeostasis.

Osseointegration occurs when cells in the peri-implant space attach to the implant surface and differentiate into matrix-secreting osteoblasts. In our implant model, peri-implant cells originate from the endosteum and bone marrow cavity; consequently, our first objective was to identify cells in these regions that were capable of responding to a Wnt stimulus. Axin2 is a direct, cell-type independent target of Wnt signaling. In Axin2$^{LacZ/+}$ mice, LacZ expression is driven by Axin2 regulatory sequences and the LacZ product, beta galactosidase, is detectable by Xgal staining. Therefore, Axin2$^{LacZ/+}$ mice function as in vivo reporters of Wnt signaling activity in the bone marrow cavity.

Using Axin2$^{LacZ/+}$ mice we found that the endosteal surfaces in the adult skeleton (FIG. 1A) were populated by Xgal positive cells (FIG. 1B). Wnt responsive cells also covered the surfaces of bone trabeculae projecting into the marrow cavity (FIG. 10). Some, but not all, Wnt responsive cells co-localized with sites of alkaline phosphatase (ALP) activity (FIG. 1D), an early marker of osteoprogenitor cell differentiation.

Wnt/ß-catenin signaling controls the differentiation and activity of osteoclasts but we found minimal overlap between tartrate resistant acid phosphatase (TRAP) activity and Xgal-positive staining in the endosteum (FIG. 1E). Pericytes and endothelial cells have also been reported to be responsive to Wnt signals, but immunostaining for collagen type IV and platelet endothelial cell adhesion molecule (PECAM) did not coincide with Xgal staining (FIG. 1F and data not shown). Using Runx2 (FIG. 1G), Collagen type I (FIG. 1H), and Osteocalcin (FIG. 1I) as molecular markers of osteo-progenitor cells and committed osteoblasts, we found that Runx2 and Oc mRNAs generally co-localized with sites of Xgal staining. Thus in an intact adult skeleton, sites of Wnt signaling corresponded most closely to sites of osteo-progenitor activity rather than osteoclast activity or endothelial cells/pericytes.

Dkk1-Mediated Endosteal Bone Resorption.

To understand the role of Wnt signaling in the endosteum, we first inhibited Wnt signaling in bones using adenoviral over-expression of the soluble Wnt antagonist Dkk1. We previously employed this strategy to transiently inhibit Wnt signaling within the adult bone marrow cavity. Control mice were treated with an adenoviral vector expressing the murine IgG2αFc fragment (Ad-Fc).

We examined control and Ad-Dkk1 treated mice on post-injection day 6 (n=3 for Ad-Fc; n=6 for Ad-Dkk1) and on post-injection day 8 (n=6 for Ad-Fc; n=8 for Ad-Dkk1). Ad-Dkk1 treatment of the bone marrow cavity dramatically increased TRAP staining on the endosteal (compare FIGS. 2A and B) and periosteal (compare FIGS. 2C and D) surfaces of all treated bones. We also noted a difference in vascularization, with Ad-Dkk1 mice showing more PECAM positive cells within the bone marrow cavity (FIG. 2E,F). Only subtle alterations in ALP activity were detectable in the endosteum (FIG. 2G,H) and periosteum (FIG. 2I,J) of Ad-Fc animals compared to the Ad-Dkk1 treated animals. Collectively, these data indicate that inhibiting endogenous Wnt signaling in the adult skeleton results in robust osteoclast activity and bone resorption.

Liposomal Wnt3a and endosteal osteo-progenitor cell responses. In recent studies we found that addition of exogenous Wnt3a protein to a skeletal injury site stimulates bone regeneration. We reasoned that the peri-implant environment was like an early injury site in that it would be populated by Wnt-responsive bone marrow-derived skeletal progenitor cells. We tested this hypothesis by placing a pin into the intramedullary space (FIG. 3A) and then delivering liposomal Wnt3a (or PBS in an identical liposomal carrier) to the peri-implant space (FIG. 3B).

Using Axin2$^{LacZ/+}$ mice we confirmed that liposomal Wnt3a treatment elicited an increase in Wnt responsiveness within the marrow cavity (compare control, FIG. 3C with D). Using RT-PCR we interrogated peri-implant tissues and found that relative to mice treated with liposomal PBS, mice treated with liposomal Wnt3a showed an up regulation in the genes encoding Runx2 and the cell proliferation marker Ki67 (24 h time point, FIG. 3E). These data indicate the liposomal Wnt treatment stimulated a subset of cells in the bone marrow cavity to proliferate and up regulate the expression of osteo-progenitor genes.

Mice treated with liposomal Wnt3a initially showed lower Collagen type I expression at the 24 h time point than mice treated with liposomal PBS (FIG. 3E) but this finding was quickly reversed: by the 48 h time point Collagen type I was significantly up regulated in peri-implant tissues treated with liposomal Wnt3a (compare control, FIG. 4A with B). In addition to increased Collagen type I expression we used picrosirius red staining and polarized light and observed a collagen-rich matrix around Wnt-treated pins, which was absent in PBS controls (FIG. 4C,D).

Liposomal Wnt3a treatment also accelerated the organization of the peri-implant extracellular matrix. In PBS controls, the peri-implant tissue at the 48 h time point closely resembled the unperturbed bone marrow (compare FIG. 4E with FIG. 1A) while the Wnt-treated peri-implant tissues already exhibited a circumferential arrangement around the pin implant (FIG. 4F). Compared with PBS-treated controls, ALP activity was also elevated in Wnt-treated samples (FIG. 4G,H). ALP and TRAP activity were co-localized in samples treated with liposomal Wnt3a, indicating active remodeling; in contrast, peri-implant tissues treated with PBS showed only very low levels of TRAP activity (FIG. 4I,J). Liposomal Wnt3a treatment also resulted in increased cell proliferation in peri-implant tissues compared to controls (FIG. 4K,L). Collectively, these data demonstrate that cells within the peri-implant space respond to liposomal Wnt3a by increasing their rate of proliferation, and accelerating their differentiation into matrix-secreting osteoblasts.

Liposomal Wnt3a and Peri-Implant Bone Formation.

Does liposomal Wnt3a result in faster bone apposition surrounding the implant? Using aniline blue staining and histomorphometric measurements we quantified the amount of new bone matrix around the pins at the 96 h time point. Compared to controls, we found that sites treated with liposomal Wnt3a exhibited more interfacial bone (FIG. 5A,B), and histomorphometric analyses demonstrated 3.77 times more bone in the Wnt treated peri-implant region compared to controls (FIG. 5C). In liposomal Wnt3a samples the newly regenerated bone was directly opposed to the pin surface; in PBS samples, peri-implant bone formation was still lacking (FIG. 5D,E).

Liposomal Wnt3a accelerated the program of interfacial bone healing. At this 96 h time point ALP (FIG. 5F) and TRAP activity (FIG. 5H) were finally co-expressed in PBS-treated samples. Liposomal Wnt3a samples continued to show evidence of ALP (FIG. 5G) and TRAP activity (FIG. 5I), indicating that active bone remodeling is supported by Wnt treatment. Thus, liposomal Wnt3a treatment accelerates interfacial bone deposition and remodeling around a pin implant.

Liposomal Wnt3a and maintenance of the osseointegration state. At early stages of osseointegration, liposomal Wnt3a treatment accelerates bone formation but is this advantage maintained at later time points? To answer this question we collected tibiae two weeks after pin placement and used aniline blue staining (FIG. 6A,B) and histomorphometric measurements to assess the amount of bone that remained around the pins. We found that mice treated with liposomal Wnt3a still had significantly more peri-implant bone than PBS-treated controls (FIG. 6C). Both control and Wnt-treated samples still showed continued evidence of bone remodeling by ALP (FIGS. 6D,E) and TRAP activity (FIG. 6F,G) but there was another compelling difference between the two groups: PBS-treated samples still had a band of fibrous connective tissue (marked by asterisks in FIG. 6H; also see asterisks in FIG. 6A) that separated the mineralized osteoid matrix and the pin surface. In contrast, Wnt-treated samples exhibited a mineralized osteoid matrix in tight proximity to the pin surface (FIG. 6I). An abundant literature indicates that this interfacial bone is directly responsible for implant stability.

It has become increasingly clear that biological approaches may be beneficial for implant osseointegration, including the Wnt family of secreted growth factors. The ability to purify Wnt proteins and package them for in vivo use has provided a unique opportunity to directly test Wnt protein as an osteo-inductive agent for osseointegration.

Endogenous Wnt signaling regulates multiple phases of the skeletogenic program but it is unsagacious to assume that the function of Wnt signaling would be equivalent among all of these cell types and across all of these stages of skeletogenic differentiation. To that end, we first identified the Wnt responsive cells that exist within the peri-implant environment, then directly tested the effects of inhibiting Wnt signaling in that same location, and at that same developmental age.

Figure 1:
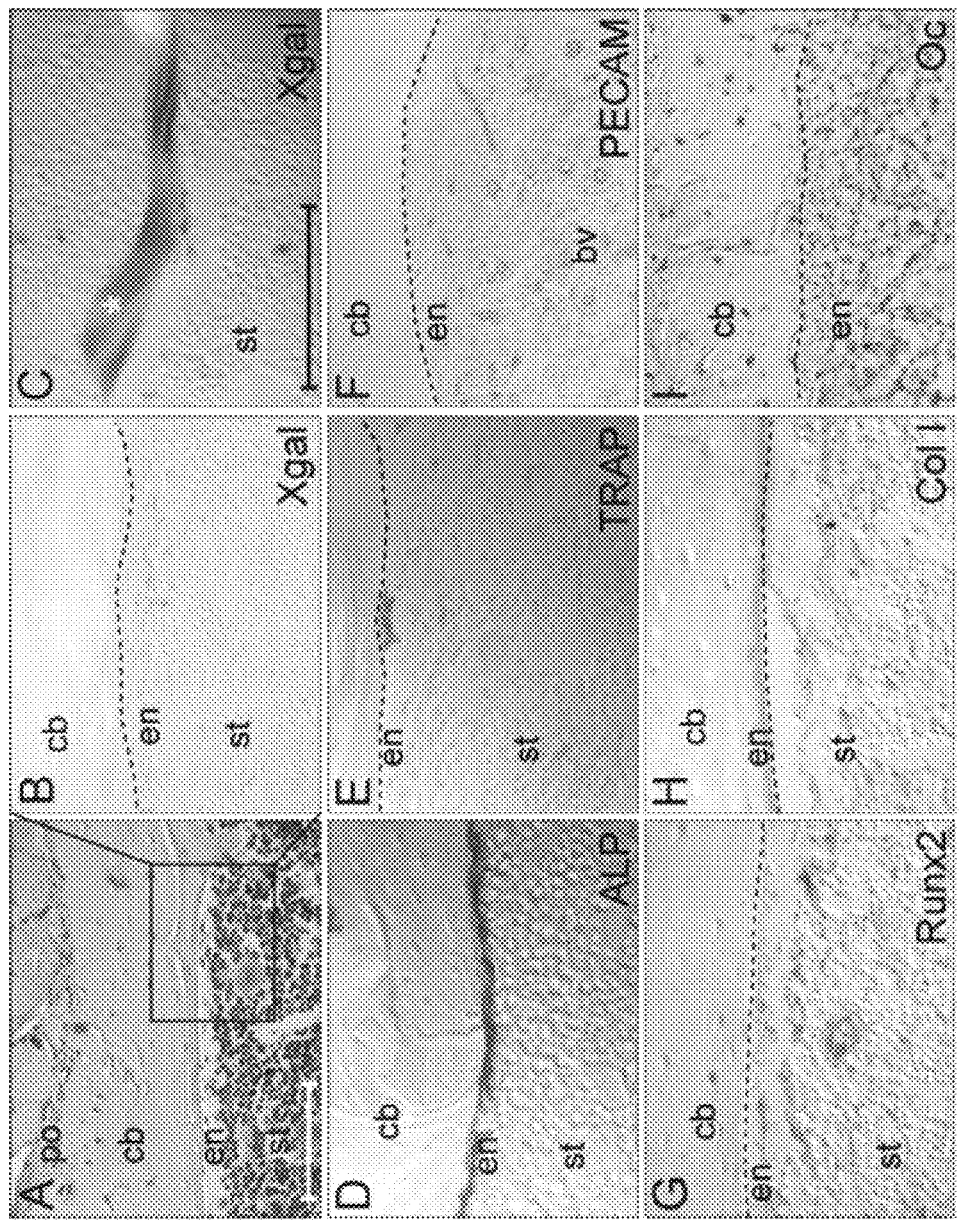
FIG. 1. Wnt responsive osteo-progenitor cells populate the endosteal surface. A) Pentachrome staining of periosteal and endosteal surfaces adult tibiae, sectioned in the transverse plane. B) Xgal staining of the tibia from an adult $Axin2^{LacZ/+}$ mouse identifies the endosteum as a site of endogenous Wnt signaling. C) Cells lining the bony trabeculae exhibit Xgal staining. D) Cells on the endosteal surface exhibit alkaline phosphatase (ALP) activity. E) Very few cells exhibit tartrate resistance acid phosphatase (TRAP) activity on the endosteal surfaces. F) Platelet endothelial cell adhesion molecule (PECAM) immunopositive cells are detected throughout the bone marrow cavity. In situ hybridization for G) Runx2, H) Collagen type I (Col I), and I) Osteocalcin (Oc) in the endosteum and bone marrow cavity of the tibia. Abbreviations: by, blood vessel; cb, cortical bone; en, endosteum; po, periosteum, *trabeculae projecting into the marrow cavity. Scale bar for all panels except C=50 µm; in C, =10 µm.

We find that cells in the fibrous periosteum and cells lining the endosteal surfaces of long bones retain their Wnt responsiveness throughout adulthood (FIG. 1). We were particularly interested in the identities of the Wnt responsive cells within the bone marrow cavity. Wnt responding cells are identifiable using Xgal staining of $Axin2^{LacZ/+}$ tissue sections and for the most part, Xgal staining patterns overlapped with the staining patterns for ALP activity (FIG. 1). The co-expression of a number of osteogenic genes further suggested that most Wnt responsive cells in the adult skeleton are part of the osteo-progenitor lineage. In addition, there is growing evidence that a population of Wnt responsive cells within the bone marrow cavity actually comprise the osteoblast stem cell niche. If true, then in addition to their contribution to bone regeneration these marrow-derived Wnt responsive cells should be able to contribute to the repair of cartilage, muscle, and connective tissue injuries.

Figure 2:
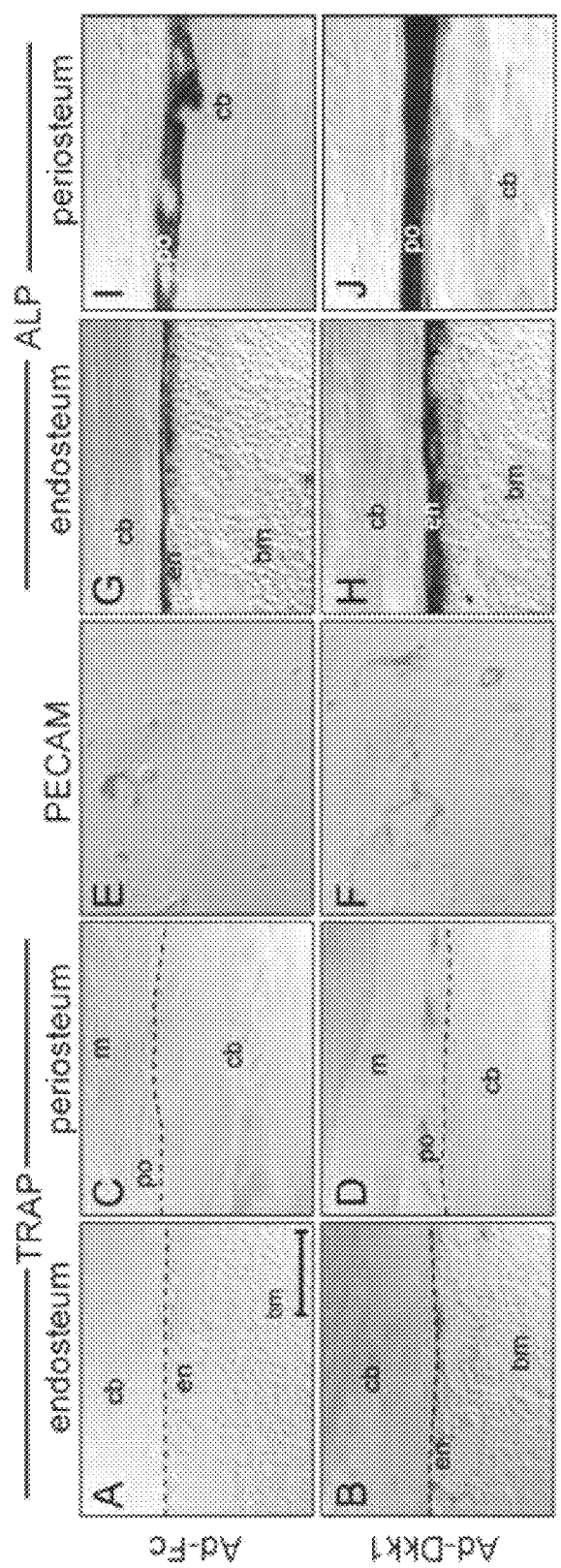
FIG. 2: Inhibition of Wnt signaling results in bone resorption. A) Tartrate resistance acid phosphatase (TRAP) activity in the endosteum, 48 h after injection of a control adenovirus that expresses the coding region of IgG2α Fc. B) TRAP activity in the endosteum, 48 h after injection of adenovirus expressing coding region for Dkk1. C) TRAP activity of periosteum from control tibiae at 48 h time point. D) TRAP activity of periosteum from Ad-Dkk1 injected tibiae, 48 h time point. E) Platelet endothelial adhesion molecule (PECAM) staining in bone marrow after injection of Ad-Fc control, 48 h time point. F) PECAM staining in bone marrow after Ad-Dkk1 delivery, 48 h time point. G) Alkaline phosphatase (ALP) activity of endosteum after Ad-Fc injection. H) ALP activity of endosteum after Ad-Dkk1 injection. I) ALP activity of periosteum after injection of Ad-Fc. J) ALP activity of periosteum after delivery of Ad-Dkk1. Abbreviations: bm, bone marrow; cb, cortical bone; po, periosteum; m, muscle. Scale bar for all panels=50 µm.

When endogenous Wnt signaling is blocked by overexpression of the Wnt inhibitor Dkk1, we find a dramatic increase in osteoclastic bone resorption (FIG. 2). A similar finding occurs in humans with multiple myeloma, where the severe osteolysis and pathological bone resorption is attributed to Dkk1-mediated inhibition in Wnt signaling in the bone marrow cavity. In some experimental models of multiple myeloma bone resorption can be blocked by function-blocking anti-Dkk1 antibodies. Bone resorption can also be reversed by subsequent delivery of conditioned media from Wnt-expressing cells. This is in keeping with our data showing that liposomal Wnt3a stimulates bone regeneration within the bone marrow cavity.

Wnt Signaling and Adult Bone Homeostasis.

Figure 3:
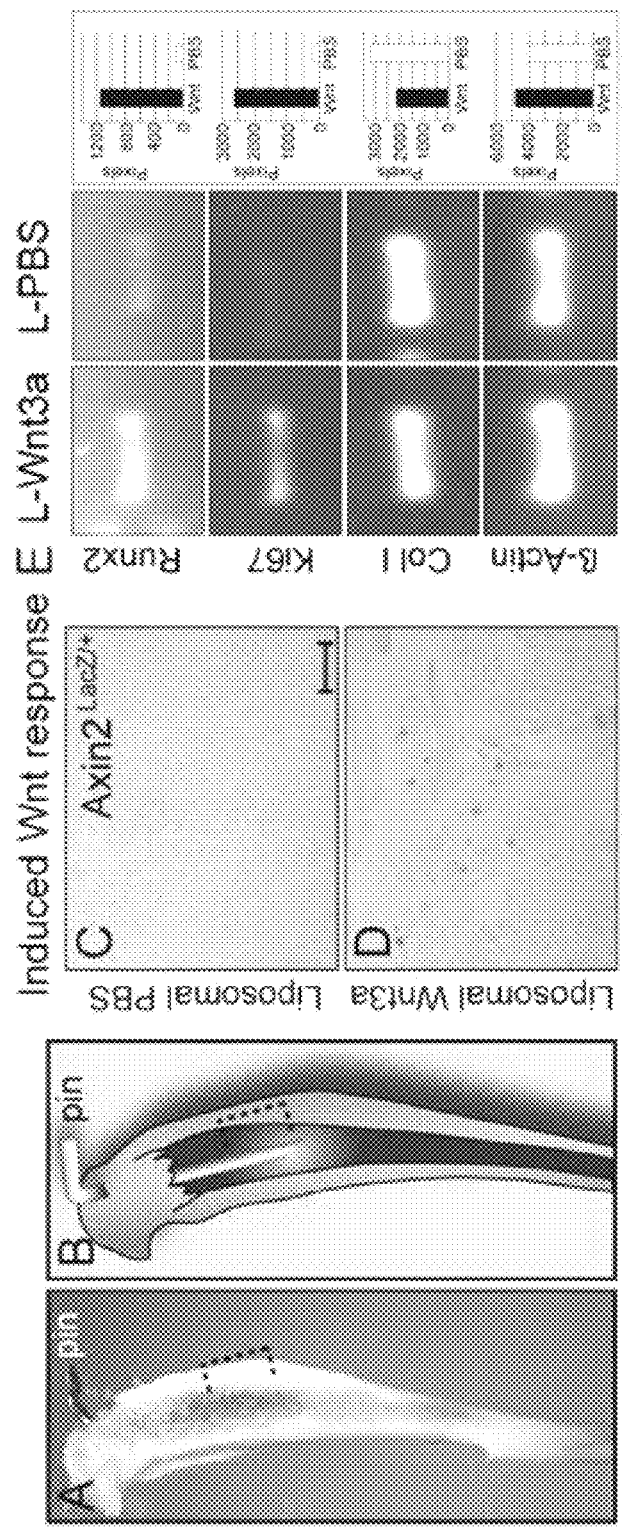
FIG. 3: liposomal Wnt3a stimulates osteoprogenitor cell proliferation A) Murine tibia with pin implant in place; the injection of methylene blue dye indicates position of implant tip. B) Scheme depicting position of pin implant into the tibia. Dotted line indicates the region of tissue analysis. C) Xgal staining of cells in the bone marrow cavity of $Axin2^{LacZ/+}$ mice, 24 hours after injection of PBS liposomes, and D) liposomal Wnt3a. E) RT-PCR of peri-implant tissues collected 24 h after injection of liposomal Wnt or liposomal PBS. ImageJ software was used for quantification of band intensity. Abbreviations: bm, bone marrow. Scale bar for panels C and D=100 µm.

Injury stimulates endogenous Wnt signaling. This injury response is highly conserved throughout evolution and is essential for even the most primitive of healing responses. Liposomal Wnt3a treatment transiently amplifies the normal Wnt response to injury, which occurs after fractures, drilling, and most importantly for this work, implant placement (FIG. 3). Wnt signaling is necessary for bone formation in the marrow cavity, but a key feature of this pro-osteogenic response is its duration. We found that a constant Wnt signal, caused by an activating mutation in the Wnt Lrp5 receptor, is detrimental for adult bone healing after injury due to an uncontrolled proliferative response from osteo-progenitor cells in the wound site. Therefore, an approach that makes use of the Wnt pathway to stimulate implant osseointegration must take into account the strict temporal and spatial duration of Wnt signaling.

Augmentation of Bone Formation with Liposomal Wnt3a.

Figure 5:
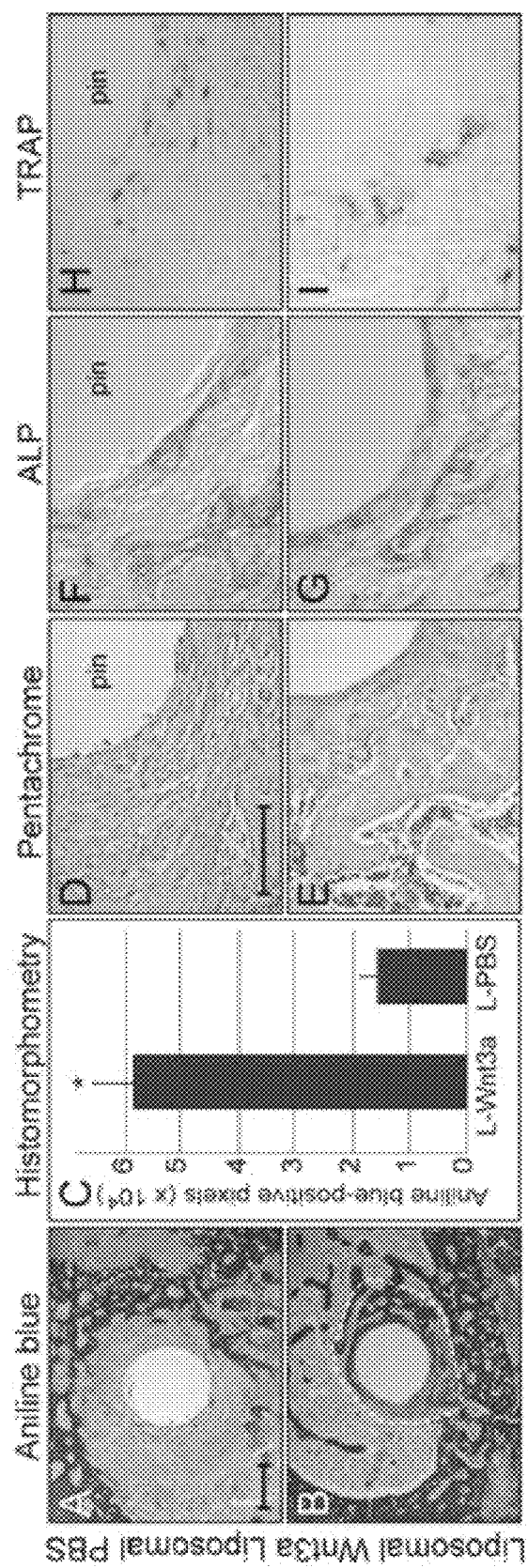
FIG. 5: Liposomal Wnt3a increases in interfacial bone formation After 4 days, A) aniline blue staining of interfacial bone in samples treated with liposomal PBS or B) liposomal Wnt3a. C) Quantification of aniline blue-stained interfacial bone on post-injection day 4 (n=3 for liposomal Wnt3a, n=3 for liposomal PBS). D) Pentachrome histology, in which bone matrix stains yellow, seen treatment with liposomal PBS or E) liposomal Wnt3a. F) Alkaline phosphatase (ALP) activity after liposomal PBS or G) liposomal Wnt3a. H) Tartrate resistance acid phosphatase (TRAP) activity after liposomal PBS or I) liposomal Wnt3a. Scale bar for panels A and B=100 µm, all other panels=50 µm.
Figure 6:
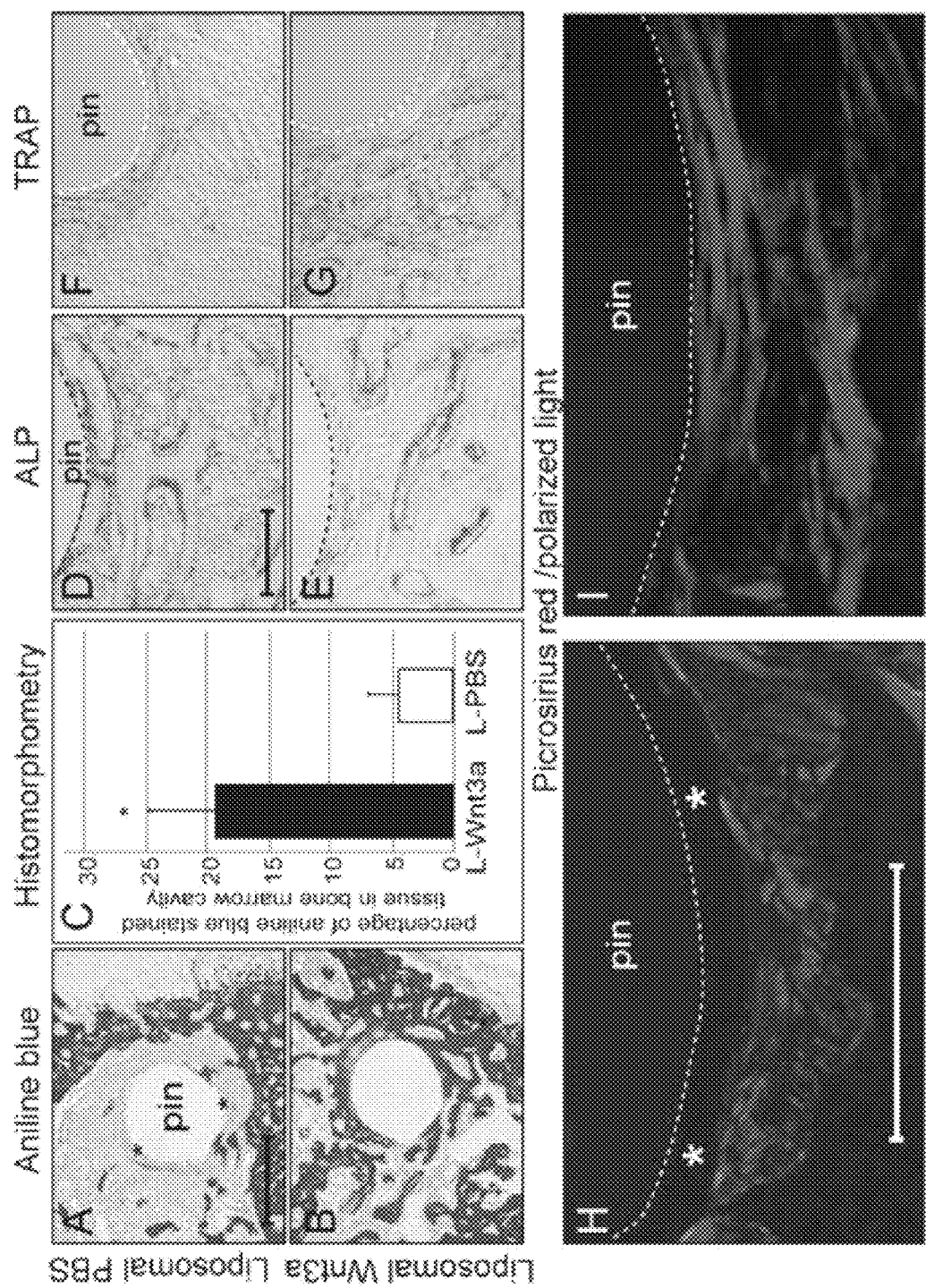
FIG. 6: The osteogenic advantage conferred by liposomal Wnt3a is maintained at later stages of implant osseointegration. Eleven days after treatment A) aniline blue staining of the interfacial bone formed after liposomal PBS or B) liposomal Wnt3a. C) Quantification of interfacial bone by aniline blue staining and histomorphometric analyses (n=2 for each condition, p<0.01). D) Alkaline phosphatase (ALP) activity after liposomal PBS or E) liposomal Wnt3a. F) Tartrate resistance acid phosphatase (TRAP) activity after liposomal PBS or G) liposomal Wnt3a. H) Picrosirius red staining for collagen matrix after treatment with liposomal PBS or I) liposomal Wnt3a. Asterisk denotes cells—but no collagen matrix—that occupies the peri-implant space. Scale bar for panels A and B=200 µm, panels D, E, F and G=50 µm, panels H and I=10 µm.

We find that liposomal Wnt3a treatment up regulates transcription of a Wnt-dependent LacZ transgene in peri-implant tissues, and stimulates the proliferation of Runx2-expressing cells (FIG. 3). Twenty-four hours after delivery, we find that liposomal Wnt-treated tissues show higher levels of Collagen type I expression and the deposition of a collagenous mineralized matrix (FIG. 4), which by post-treatment day 4 has resulted in almost 3.8 times more peri-implant bone than controls (FIG. 5). Even at later stages, we find an osteogenic advantage of having treated an implant site with liposomal Wnt3a (FIG. 6). The optimal time for Wnt treatment in this system was found to be three days following implantation.

Figure 7:
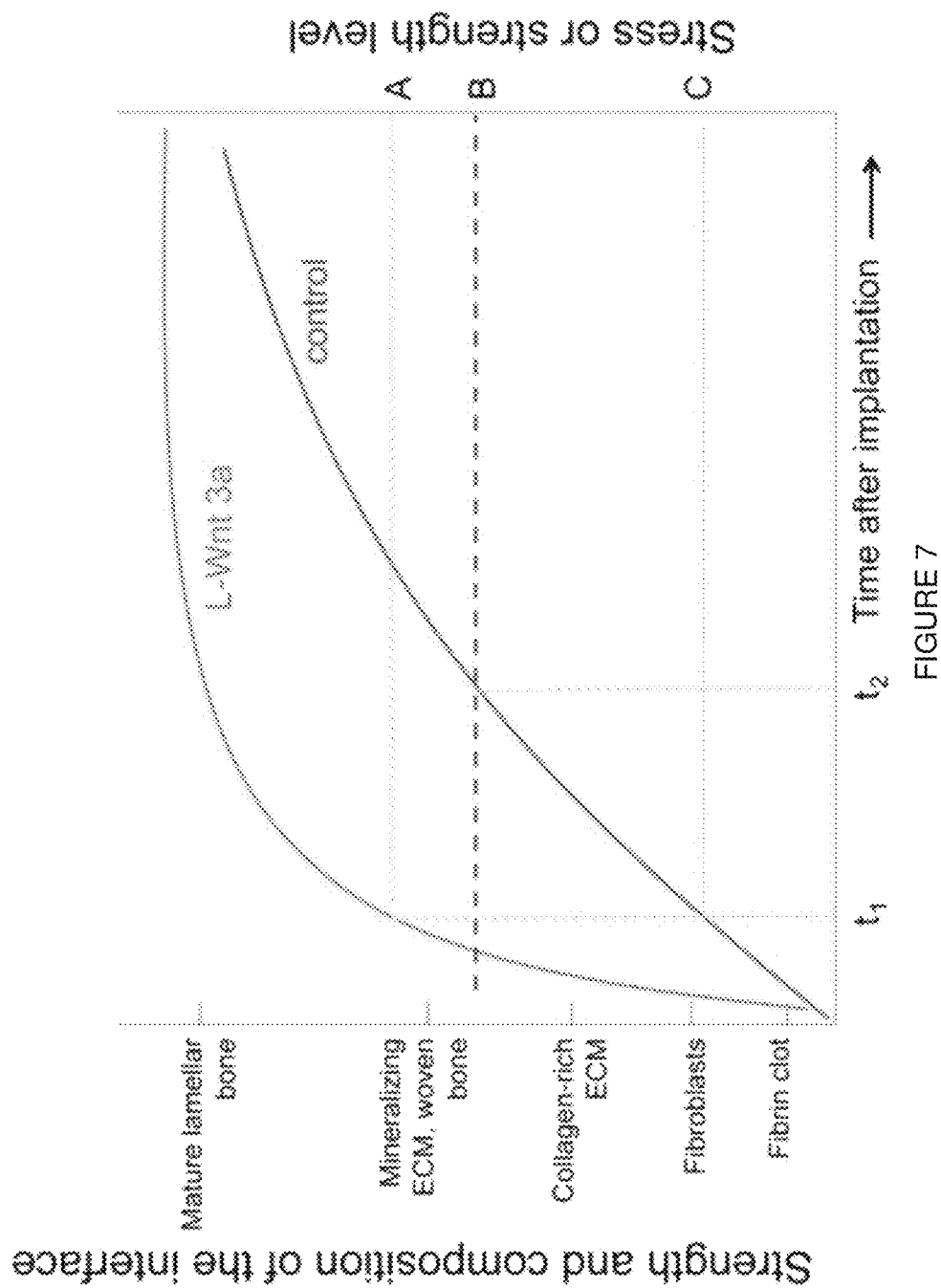
FIG. 7: Treatment with liposomal Wnt3a creates a margin of safety which allows for the protection against implant failure. As healing progresses, the composition and strength of the interface (with or without L-Wnt3a) ranges from that of fibrin all the way up to that of fully-dense lamellar bone. However, administration of L-Wnt3a leads to achievement of a larger strength of the interface (A) than for the control case (C) at a chosen post-surgical time, say $t_1$. Therefore, if implant loading were to begin at post-surgical time $t_1$ and produced an interfacial stress level B (purple dotted line), then stress B will be less than strength A of the L-Wnt3a interface but greater than strength C of the control interface; this means that at time $t_1$, interface C will fail, but not interface A. In this example, the safety factor for interface A is therefore the ratio A/B. Another view of the situation is to observe that one needs to wait until just beyond time $t_2$ before loading the control interface to a stress B, because only then would the control interface have achieved a strength that's larger than stress B. The time difference $t_2-t_1$ represents how much earlier one could load the interface treated with L-Wnt3a with a stress level B. One interesting additional point is that, in general, any implant will typically produce a rather complicated, spatially-varying stress state in the interface, due to geometric irregularities of the implant, placement in the surgical site, and variations in how it is loaded during function. Therefore, the schematic plot in FIG. 7 is expected to differ from place to place in the interface because the applied stress level B will also differ from place to place.

Biomechanical safety margin. A biomechanical safety margin would provide a measure of protection that could have significant long-term benefits over the lifespan of an implant. When bone forms more rapidly and with higher density after an implant is placed, the implant is more effectively shielded from excessive strain (FIG. 7). As healing progresses, the composition and strength of the interface ranges from that of fibrin all the way up to that of dense lamellar bone. The administration of liposomal Wnt3a leads to a stronger implant-tissue interface at an earlier time point than for control cases. Therefore, a safety margin is created, because at any given post surgical time, liposomal Wnt3a offers an advantage of increased strength that may be enough to prevent the implant failure that would otherwise be likely in a control case. This safety margin not only protects from implant failure at certain loads, but also allows the implant to be loaded at an earlier time point.

The lifespan of an implant is largely determined by the untoward effects of wear debris and excessive loading, both of which are characterized by a shift in peri-implant tissues away from a mineralized bone tissue towards a fibrous or fibrocartilaginous tissue. The fibrous encapsulation of a failed implant demonstrates that peri-implant space retains the capacity to de-differentiate from matrix-secreting osteo-blasts into fibrous or fibrocartilaginous cell types. Our data demonstrate that transient exposure to a Wnt3a stimulus induces peri-implant cells to rapidly adopt an osteogenic cell fate. After removal of excessive forces, this fibrous tissue could be converted into bony tissue by exposing peri-implant cells to liposomal Wnt3a.

What is claimed is:

1. A method of inducing osteogenesis at an implant site in a mammal undergoing dental or orthopedic implantation, the method comprising:
   administering to the mammal at the implant site a therapeutically effective dose of a Wnt3A polypeptide,
   wherein the Wnt3A polypeptide is inserted in the non-aqueous phase of a liposome;
   wherein the Wnt3A polypeptide is conjugated to a lipid moiety within the liposome;
   wherein the liposome has a size from 100 nm to 200 nm;
   wherein the Wnt3A polypeptide is administered once to the mammal by injection at the site of the implant; and
   wherein the Wnt3A polypeptide induces osteogenesis, and the osteogenesis is maintained for at least 11 days.

2. The method of claim 1, wherein the implant site is the site of a bone injury.

3. The method of claim 1, wherein the implant site is the site of an orthopedic implant.

4. The method of claim 1, wherein the implant site is the site of a dental implant.

5. The method of claim 4, wherein the implant site is a peri-implant space.

6. The method of claim 1, wherein the Wnt3A polypeptide is administered within 5 days after introduction of the implant.

7. The method of claim 1, wherein the Wnt3A polypeptide is administered within 3 days after introduction of the implant.

8. The method of claim 2, wherein the Wnt3A polypeptide is administered within 3 days of the injury.

9. The method of claim 1, wherein the mammal is a human.

10. The method of claim 9, wherein the Wnt3A polypeptide is human Wnt3A polypeptide.

11. A method of inducing osteogenesis at a failed implant site in a mammal, the method comprising:

administering to the mammal at the failed implant site a therapeutically effective dose of a Wnt3A polypeptide, wherein the Wnt3A polypeptide is inserted in the non-aqueous phase of a liposome;

wherein the Wnt3A polypeptide is conjugated to a lipid moiety within the liposome;

wherein the liposome has a size from 100 nm to 200 nm;

wherein the Wnt3A polypeptide is administered once to the mammal by injection at the site of the failed implant; and wherein the Wnt3A polypeptide induces osteogenesis, and the osteogenesis is maintained for at least 11 days.

12. The method of claim 11, wherein the Wnt3A polypeptide is human Wnt3A polypeptide.

* * * * *

UNITED STATES PATENT AND TRADEMARK OFFICE
CERTIFICATE OF CORRECTION

Page 1 of 1

PATENT NO. : 10,183,057 B2
APPLICATION NO. : 14/337718
DATED : January 22, 2019
INVENTOR(S) : Jill Helms et al.

It is certified that error appears in the above-identified patent and that said Letters Patent is hereby corrected as shown below:

In the Specification

Please insert the paragraph in Column 1, immediately after the title, to read as follows:
-- GOVERNMENT SUPPORT RESEARCH
This invention was made with Government support under contract DE024000 awarded by the National Institutes of Health. The Government has certain rights in the invention. --

Signed and Sealed this
Eleventh Day of November, 2025

John A. Squires
*Director of the United States Patent and Trademark Office*

SEQUENCE LISTING

```
<160> NUMBER OF SEQ ID NOS: 10

<210> SEQ ID NO 1
<211> LENGTH: 20
<212> TYPE: DNA
<213> ORGANISM: Homo sapiens

<400> SEQUENCE: 1
catgtcgtcc cagttggtaa                                               20

<210> SEQ ID NO 2
<211> LENGTH: 20
<212> TYPE: DNA
<213> ORGANISM: Homo sapiens

<400> SEQUENCE: 2
gccagccccg ctgatacacc                                               20

<210> SEQ ID NO 3
<211> LENGTH: 20
<212> TYPE: DNA
<213> ORGANISM: Homo sapiens

<400> SEQUENCE: 3
ttccctggag actggggcca                                               20

<210> SEQ ID NO 4
<211> LENGTH: 21
<212> TYPE: DNA
<213> ORGANISM: Homo sapiens

<400> SEQUENCE: 4
gcctcccaga acatcaccta t                                             21

<210> SEQ ID NO 5
<211> LENGTH: 18
<212> TYPE: DNA
```

```
<213> ORGANISM: Homo sapiens

<400> SEQUENCE: 5
aattcctggt ctggggca                                                   18

<210> SEQ ID NO 6
<211> LENGTH: 40
<212> TYPE: DNA
<213> ORGANISM: Homo sapiens

<400> SEQUENCE: 6
attaaccctc actaaaggga cccacggccc tccctgaact                           40

<210> SEQ ID NO 7
<211> LENGTH: 40
<212> TYPE: DNA
<213> ORGANISM: Homo sapiens

<400> SEQUENCE: 7
taatacgact cactataggg gccgagggac atgcctgacg                           40

<210> SEQ ID NO 8
<211> LENGTH: 21
<212> TYPE: DNA
<213> ORGANISM: Homo sapiens

<400> SEQUENCE: 8
ttgataaggt cctggcaact c                                               21

<210> SEQ ID NO 9
<211> LENGTH: 18
<212> TYPE: DNA
<213> ORGANISM: Homo sapiens

<400> SEQUENCE: 9
gcgaacggct gcttattt                                                   18

<210> SEQ ID NO 10
<211> LENGTH: 20
<212> TYPE: DNA
<213> ORGANISM: Homo sapiens

<400> SEQUENCE: 10
ggaatgggtc agaaggactc                                                 20
```